US010849868B2

(12) United States Patent
Basara et al.

(10) Patent No.: US 10,849,868 B2
(45) Date of Patent: Dec. 1, 2020

(54) FORMULATION FOR TREATING CHRONIC WOUNDS

(71) Applicant: EPIEN Medical, Inc., White Bear Lake, MN (US)

(72) Inventors: Michael Basara, Hugo, MN (US); Matthew J. Watkins, Elk River, MN (US); James Bracke, Vadnais Heights, MN (US)

(73) Assignee: EPIEN Medical, Inc., White Bear Lake, MN (US)

( * ) Notice: Subject to any disclaimer, the term of this patent is extended or adjusted under 35 U.S.C. 154(b) by 14 days.

(21) Appl. No.: 15/508,306

(22) PCT Filed: Sep. 2, 2015

(86) PCT No.: PCT/US2015/048172
§ 371 (c)(1),
(2) Date: Mar. 2, 2017

(87) PCT Pub. No.: WO2016/036871
PCT Pub. Date: Mar. 10, 2016

(65) Prior Publication Data
US 2017/0281572 A1 Oct. 5, 2017

Related U.S. Application Data

(60) Provisional application No. 62/044,650, filed on Sep. 2, 2014.

(51) Int. Cl.
| | | |
|---|---|---|
| *A61K 31/185* | (2006.01) | |
| *A61K 33/04* | (2006.01) | |
| *A61K 47/02* | (2006.01) | |
| *A61K 9/00* | (2006.01) | |
| *A61K 9/08* | (2006.01) | |
| *A61P 31/04* | (2006.01) | |
| *A61P 17/02* | (2006.01) | |

(52) U.S. Cl.
CPC .......... *A61K 31/185* (2013.01); *A61K 9/0014* (2013.01); *A61K 9/08* (2013.01); *A61K 33/04* (2013.01); *A61K 47/02* (2013.01); *A61P 17/02* (2018.01); *A61P 31/04* (2018.01)

(58) Field of Classification Search
CPC ........ A61K 47/02; A61K 31/185; A61K 9/08; A61K 31/04; A61K 33/04; A61K 9/0014
See application file for complete search history.

(56) References Cited

U.S. PATENT DOCUMENTS

| | | | |
|---|---|---|---|
| 5,939,090 A | 8/1999 | Beaurline et al. | |
| 7,132,111 B2 * | 11/2006 | Basara | A61K 8/466 424/434 |
| 2003/0069317 A1 * | 4/2003 | Seitz, Jr. | A01N 31/08 514/731 |
| 2004/0132810 A1 | 7/2004 | Basara | |
| 2005/0142208 A1 | 6/2005 | Yoo et al. | |
| 2007/0005026 A1 | 1/2007 | Basara et al. | |
| 2007/0025927 A1 * | 2/2007 | Basara | A61K 8/466 424/49 |
| 2007/0191793 A1 * | 8/2007 | Basara | A61L 2/0082 604/289 |
| 2009/0202457 A1 | 8/2009 | Basara | |
| 2011/0245757 A1 * | 10/2011 | Myntti | A61K 31/19 604/22 |
| 2013/0101627 A1 | 4/2013 | Tieu et al. | |
| 2016/0058718 A1 | 3/2016 | Basara et al. | |

FOREIGN PATENT DOCUMENTS

| | | |
|---|---|---|
| WO | WO-2004062580 A2 | 7/2004 |
| WO | WO-2007002194 A2 | 1/2007 |
| WO | WO-2016036871 A1 | 3/2016 |

OTHER PUBLICATIONS

Werdin et al., Evidence-based Management Strategies for Treatment of Chronic Wounds, ePlasty, pp. 169-179 . . . (Year: 2009).*
"U.S. Appl. No. 14/843,658, Non Final Office Action dated Apr. 8, 2016", 9 pgs.
"International Application Serial No. PCT/US2015/048172, International Preliminary Report on Patentability dated Mar. 16, 2017", 11 pgs.
"International Application Serial No. PCT/US2015/048172, International Search Report dated Oct. 29, 2015", 4 pgs.
"International Application Serial No. PCT/US2015/048172, Written Opinion dated Oct. 29, 2015", 9 pgs.
Davis, S C, et al., "Cosmeceuticals and natural products", wound healing, Clinics in Dermatology,, (2009), 502-506.
"European Application Serial No. 15838487.5, Extended European Search Report dated May 7, 2018", 7 pgs.
"European Application Serial No. 15838487.5, Response filed Dec. 11, 2017 to Action dated Jun. 1, 2017", 27 pgs.
"European Application Serial No. 15838487.5, Response filed Dec. 4, 2018 to Extended European Search Report dated May 7, 2018", 52 pgs.
"European Application Serial No. 15838487.5, Communication pursuant to Article 94(3) EPC dated Feb. 22, 2019", 5 pgs.
"European Application Serial No. 15838487.5, Communication Pursuant to Article 94(3) EPC dated Jun. 19, 2020", 3 pgs.
"European Application Serial No. 15838487.5, Communication Pursuant to Article 94(3) EPC dated Aug. 13, 2019", 4 pgs.
Porter, S R, et al., "Randomised controlled trial of the efficacy of HybenX in the symptomatic treatment of recurrent aphthous stomatitis", Oral Diseases, vol. 15, No. 2, (Mar. 2009), 155-161.

* cited by examiner

*Primary Examiner* — Mina Haghighatian
(74) *Attorney, Agent, or Firm* — Schwegman Lundberg & Woessner, P.A.

(57) ABSTRACT

Inventive subject matter disclosed herein includes a method of treating a chronic wound. The method includes mechanically debriding a chronic wound; and applying a formulation to the wound for 5 to 60 seconds, the formulation including: phenolsulfonic acid—37% by weight; guaiacolsulfonic acid—24% by weight; free sulfuric acid—29% by weight; and water—10% by weight.

8 Claims, 4 Drawing Sheets

FORMULATION FOR TREATING CHRONIC WOUNDS

CROSS-REFERENCE TO RELATED APPLICATION

The present application is a U.S. National Stage Filing under 35U.S.C. 371 from International Application No. PCT/US2015/048172, filed Sep. 2, 2015, which claims the benefit of U.S. provisional application Ser. No. 62/044,650, filed Sep. 2, 2014, which applications are incorporated by reference herein their entirety.

FIELD

Inventive subject matter disclosed herein relates to formulation and method embodiments for treating chronic wounds and for preventing and treating bacterial infections.

BACKGROUND

Wounds, such as chronic wounds that do not heal, pose a vexing problem for patients and health professionals. These wounds include, but are not limited to chronic venous leg ulcers, pressure ulcers, diabetic ulcers, decubitus ulcers, stasis ulcers, dermal ulcers, burns, and pressure ulcers. Chronic wounds are characterized by necrotic tissue that delays healing. Necrotic tissue may act as a reservoir for bacterial growth. Necrotic tissue also contains inflammatory mediators that promote inflammation and impair cellular migration.

Conventional treatment for chronic wounds includes debridement that attempts to remove the necrotic tissue. Debridement may be autolytic, enzymatic, mechanical, surgical, and, in some instances, performed with maggots. None of these conventional debridement treatments has been successful in healing chronic wounds.

SUMMARY

Figure 1:
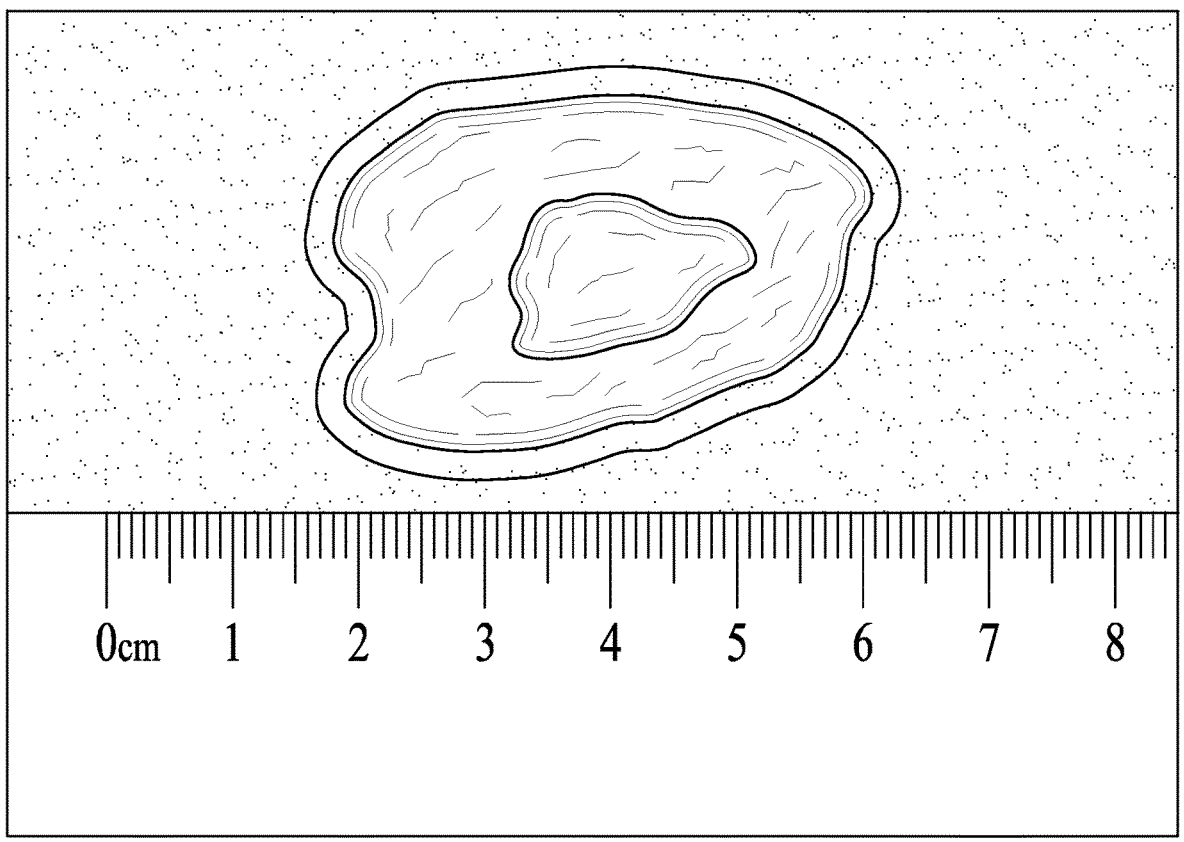
FIG. 1 is a top plan view of a chronic wound prior to treatment.
Figure 2:
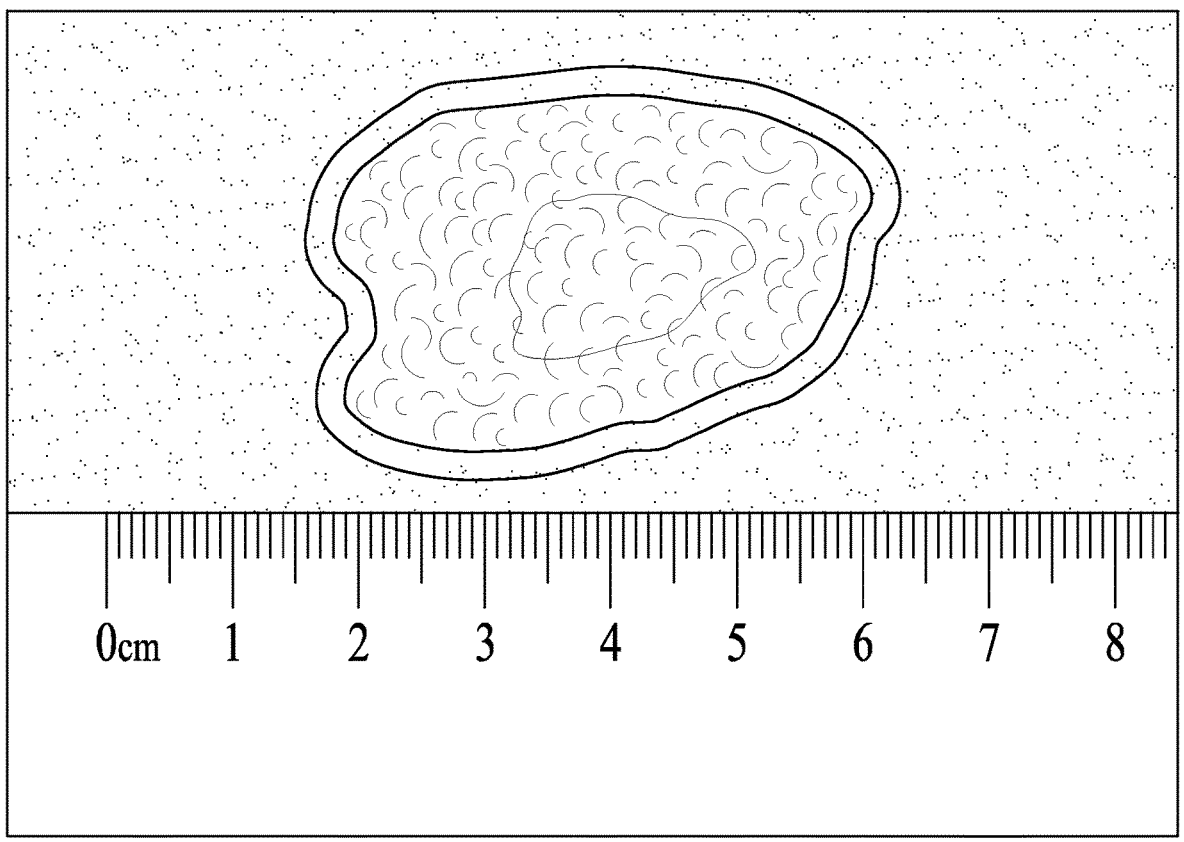
FIG. 2 is a top plan view of the chronic wound of FIG. 1 one week after a treatment, using a formulation embodiment of the present invention.
Figure 3:
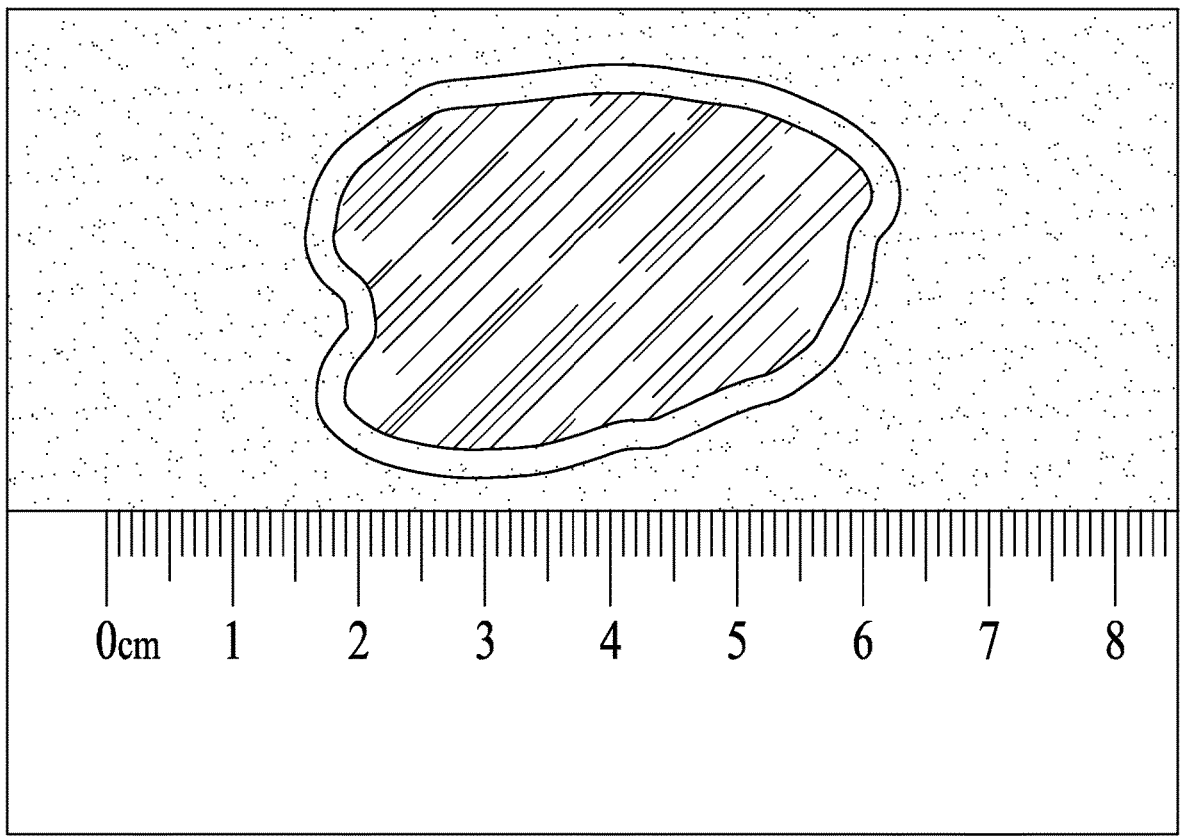
FIG. 3 is a top plan view of the chronic wound of FIG. 1 two weeks after a treatment, using the formulation embodiment of the present invention used in FIG. 2.

One embodiment of the present invention is a liquid formulation for treating chronic wounds. The liquid formulation includes the following:
  phenolsulfonic acid—37% by weight;
  guaiacolsulfonic acid—24% by weight;
  free sulfuric acid—29% by weight; and
  water—10% by weight
Another embodiment includes a gel formulation for treating chronic wounds. The gel formulation includes the following:
  phenolsulfonic acid—36% by weight;
  guaiacolsulfonic acid—23% by weight;
  free sulfuric acid—28% by weight;
  water—10% by weight; and
  colloidal silica—3% by weight.
Another embodiment includes a liquid formulation for treating chronic wounds. The embodiment includes the following:
  benzenesulfonic acid—45% by weight;
  phenolsulfonic acid—40% by weight; and
  water—15% by weight.
Another embodiment includes a gel formulation for treating chronic wounds. The gel includes the following:
  benzenesulfonic acid—43% by weight;
  phenolsulfonic acid—38% by weight;
  water—14% by weight; and
  colloidal silica—5% by weight.
Another embodiment includes a liquid formulation for treating chronic wounds. The formulation includes the following components and concentration ranges:
  phenolsufonic acid (10-75% wt. percent);
  guaiacolsulfonic acid (10-75% wt. percent);
  free sulfuric acid (0-30% wt. percent);
  water (0-30% wt. percent); and
  colloidal silica (0-10% wt. percent).
Another formulation embodiment for treating chronic wounds, includes the following components and concentration ranges:
  benzenesulfonic acid (10-75% by weight);
  phenolsulfonic acid (10-75% by weight);
  water (0-30% by weight); and
  colloidal silica (0-10% by weight).
Another embodiment is a method of treating a chronic wound, that includes:
  applying a formulation to the wound for 5 to 60 seconds, the formulation comprising:
  phenolsulfonic acid—37% by weight; guaiacolsulfonic acid—24% by weight; free sulfuric acid—29% by weight; and water—10% by weight.
Another embodiment is a method for treating a chronic wound, that includes:
  applying a formulation to the wound for 5 to 60 seconds, the formulation comprising: gel formulation for treating chronic wounds, that includes:
  phenolsulfonic acid—36% by weight;
  guaiacolsulfonic acid—23% by weight;
  free sulfuric acid—28% by weight;
  water—10% by weight; and
  colloidal silica—3% by weight.
Another embodiment includes a method of treating a chronic wound, that includes:
  applying a formulation to the wound for 5 to 60 seconds, the formulation comprising: A liquid formulation for treating chronic wounds, that includes:
  benzenesulfonic acid—45% by weight;
  phenolsulfonic acid—40% by weight; and
  water—15% by weight.
Another embodiment includes a method of treating a chronic wound, that includes:
  applying a formulation to the wound for 5 to 60 seconds, the formulation comprising:
  a gel formulation for treating chronic wounds, that includes:
  benzenesulfonic acid—43% by weight;
  phenolsulfonic acid—38% by weight;
  water—14% by weight; and
  colloidal silica—5% by weight.
Another embodiment includes a method of treating a chronic wound, that includes:

applying a formulation to the wound for 5 to 60 seconds, the formulation that includes:
a liquid formulation for treating chronic wounds, that includes:
phenolsufonic acid (10-75% wt. percent);
guaiacolsulfonic acid (10-75% wt. percent);
free sulfuric acid (0-30% wt percent);
water (0-30% wt. percent); and
colloidal Silica (0-10% wt. percent).

Another embodiment includes a method of treating a chronic wound, including:
applying a formulation to the wound for 5 to 60 seconds, the formulation comprising:
a formulation for treating chronic wounds, including:
benzenesulfonic acid (10-75% wt. percent);
phenolsulfonic acid (10-75% wt. percent);
water (0-30% wt. percent); and
colloidal Silica (0-10% wt. percent).

Another embodiment includes a method of treating a chronic wound, including: applying a formulation to the wound for 5 to 60 seconds, the formulation comprising:
phenolsulfonic acid 25-80% by weight;
guaiacolsulfonic acid 25-80% by weight;
ammonium phenolsulfonate 0-5% by weight; and
water 13-30% by weight.

Another embodiment includes a method for preventing infections by antibiotic resistant bacteria, including: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica in a concentration of 0 to 10% by weight topically to a surface of a living being.

Another embodiment includes a method for preventing bacterial infections, including: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to a surface of a living being.

Another method embodiment for preventing bacterial infections by persistant bacteria, including: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to a surface of a living being.

Another method embodiment for preventing biofilm formation, includes: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to a surface of a living being.

Another method embodiment for treating infections by antibiotic resistant bacteria, includes: applying a formulation comprising phenolsulfonic acid in a concentration of 10-75% by weight; guiacolfonic acid in a concentration of 0-30% by weight; free sulfuric acid in a concentration of 10-30% by weight; water in a concentration of 0-30% by weight; and colloidal silica in a concentration of 0 to 10% by weight topically to a surface of a living being infected with antibiotic resistant bacteria.

Another method embodiment for treating bacterial infections, includes: applying a formulation comprising phenolsulfonic acid in a concentration of 0-75% by weight; guiacolfonic acid in a concentration of 10-30% by weight; free sulfuric acid in a concentration of 10-30% by weight; water in a concentration of 0-30% by weight; and colloidal silica by weight topically to a surface of a living being infected with a bacterial infection.

Another method embodiment for treating bacterial infections, caused by bacteria in a persistent state includes: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to a surface of a living being infected by bacteria in a persistent state.

Another method embodiment for treating biofilm infections, includes: applying a formulation comprising phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica in a concentration of 0 to 10% by weight topically to a surface of a living being contaminated by biofilm.

DETAILED DESCRIPTION

Embodiments of the invention are described in sufficient detail to enable those skilled in the art to practice the invention. Other embodiments may be utilized and structural, logical, chemical, and other changes may be made without departing from the spirit or scope of the invention discussed herein. The following detailed description is, therefore, not to be taken in a limiting sense, and the scope of the invention discussed herein is defined only by the appended claims.

Formulation embodiments disclosed herein are used as an adjunctive agent to all other forms of debridement and are compatible with all other forms of debridement. For one embodiment, the formulation embodiments are used as an adjunctive rinse following surgical debridement, also known as sharp debridement, which is a conventional form of mechanical debridement used in the treatment of chronic wounds.

Formulation embodiments include liquid and gel embodiments that, when applied to a chronic wound, effectively reduce the size of the wound and, in some instances, heal the chronic wound. It is believed that the formulations disclosed herein work by debriding the wound and by destroying biofilms and bacteria on and in a skin wound and desiccating and washing away necrotic tissue defining the chronic wound. The mechanism of action is believed to be the following: Application of a formulation embodiment disclosed herein acts as both a mechanical debridement and a chemical debridement. The mechanical debridement action derives from an elevated viscosity and density of the formulation that allows the formulation to deliver a higher level of mechanical pressure and shear stress across a surface. The chemical debridement derives from a desiccating action of the formulation embodiment which acts to destabilize the cohesion of necrotized tissues and microbial biofilm so that they are easily carried away by the mechanical action.

Formulation embodiments not only absorb water mechanically, i.e. absorb water that is adhered to microbes and biofilm within and proximal to a wound, but also absorb water that is electrostatically bonded, i.e. hydrogen bonded, with structural components of bacteria and other microbes in wounds, thereby desiccating bacterial structure and destroying bacterial structural integrity. Formulation embodiments also desiccate any residual necrotic tissue.

The mechanism of action is such that formulation embodiments do not just absorb bound water, but also absorb water that is electrostatically bonded, i.e. hydrogen bonded, with water from the structural components of bacteria, thereby destroying bacterial integrity. Additionally, formulation embodiments prevent a destructive immune response initiated by necrotizing tissue by eliminating the necrotizing tissue. Elimination prevents the body from initiating an inflammatory immune response.

Method embodiments disclosed herein are useful against bacteria, biofilm, prions, antibiotic resistant bacteria and persistent bacteria. One method embodiment for preventing infections by antibiotic resistant bacteria includes applying a formulation that includes phenolsulfonic acid in a concentration of 10-75% by weight; Guiacolfonic acid in a concentration of 10-30% by weight; free sulfuric acid in a concentration of 0-30% by weight; water in a concentration of 0-30% by weight; and colloidal silica in a concentration of 0 to 10% by weight topically to broken skin or bone or an organ surface that is at risk for infection. This method is also used in treating and killing bacteria, biofilm, prions, antibiotic resistant bacteria and persistent bacteria. All formulation embodiments disclosed herein are applicable as a spray, gel or as a solid with time release.

Another method embodiment for preventing bacterial infections includes applying a formulation that includes phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to contaminated bone.

Another method embodiment for preventing bacterial infections, includes applying a formulation that includes phenolsulfonic acid in a concentration of 10-75% by weight; guiacolfonic acid in a concentration of 10-30% by weight; free sulfuric acid in a concentration of 0-30% by weight; water in a concentration of 0-30% by weight; and colloidal silica by weight topically to a surface of a contaminated organ.

Embodiments disclosed herein are also useful against bacteria that are in a persistent state; that is bacteria that have never been cultured in a lab.

Embodiments are also useful in preventing bacterial infections in an organ.

Once structural integrity of a biofilm is destroyed by exposure to a formulation disclosed herein, the microbes die and the biofilm is disrupted. Bacteria, and other pathogens exposed to formulation embodiments disclosed herein do not develop a resistance to the formulations. Formulation and method embodiments disclosed herein are effective against all bacteria, biofilm, prions and other infectious agents.

Formulation embodiments disclosed herein are exposed to the bacterial and other pathogen structures that are desiccated by formulation embodiments disclosed herein. The structures desiccated include cell wall, plasma membrane, S-layers, glycocalyx, flagella, fimbriae and pili. Structures of both gram negative and gram positive bacteria are desiccated and susceptible to destruction. While bacteria are described, it is understood that all microbes in a biofilm are susceptible to destruction by desiccation by a formulation embodiment disclosed herein.

Additionally, formulation embodiments disclosed herein prevent damage done by a destructive inflammation immune response initiated by necrotizing tissue by eliminating the necrotizing tissue before the response is prompted. Elimination of the necrotic tissue prevents the body from initiating a destructive inflammatory immune response.

Formulation embodiments disclosed herein are effective for killing bacteria that are antibiotic resistant; such as MRSA. Formulations disclosed herein are also effective in killing bacteria that are in a persistent state. Bacteria in a persistent state are not completely immune to antibiotics but remain inactive or dormant in the presence of antibiotic treatment. Once an antibiotic regime ends, the persistent bacteria resume their activity. Recent research identified the stimulus for putting the bacteria into a persistent state which is attack by an antibiotic. The formulations disclosed herein are not conventional antibiotics and when exposed to these formulation embodiments, antibiotic resistant bacteria and bacteria in a persistent state are killed by desiccation before they enter a dormant or inactive state.

Formulation embodiments disclosed herein are also believed to kill bacteria that have not been cultured in a lab. Bacteria that have not been cultured in a lab exist in nature but do not grow on laboratory media. At the present time, these bacteria are identified by their unique genetic material. These bacteria are killed by desiccation in the manner disclosed herein.

Formulation embodiments that include free sulfuric acid have the free sulfuric acid component because sulfonation of the phenol and guaiacol or benzene performed does not remove residual sulfuric acid remaining at the conclusion of the sulfonation reactions. In order to drive the sulfonation reaction to completion so that all of the phenol and guaiacol or benzene molecules become sulfonated, excess sulfuric acid is added to a reaction mixture in a ratio of approximately 1:4:1 phenolsulfonic acid to guaiacolsulfonic acid or benzenesulfonic acid to sulfuric acid so that there is an excess of sulfuric acid when the reaction is completed. The excess sulfuric acid is referred to as "free sulfuric acid" because it is not conjugated to a phenol or guaiacol.

The formulation embodiments that do not contain any free sulfuric acid are blended from a purified sulfonated aromatic that is obtained in sulfonated form. Any residual or excess free sulfuric acid is removed, so that when blending is completed, there is substantially zero free sulfuric acid in the blend.

Specific liquid and gel formulations usable for treating wounds include the following:

Formulation 1: Contains Free Acid in a Liquid Form
    Phenolsulfonic acid—37% by weight
    Guaiacolsulfonic acid—24% by weight
    Free Sulfuric Acid—29% by weight
    Water—10% by weight Formulation 2: Contains Free Acid in a Gel Form
Product Containing Free Acid in the Gel Form
    Phenolsulfonic acid—36% by weight
    Guaiacolsulfonic acid—23% by weight
    Free Sulfuric Acid—28% by weight
    Water—10% by weight
    Colloidal Silica—3% by weight Formulation 3: Contains No Free Acid, in a Liquid Form
Product with No Free Acid in the Liquid Form
    Benzenesulfonic acid—45% by weight
    Phenolsulfonic acid—40% by weight
    Water—15% by weight Formulation 4: Contains No Free Acid, in a Gel Form
Product with No Free Acid in the Gel Form
    Benzenesulfonic acid—43% by weight
    Phenolsulfonic acid—38% by weight Water—14% by weight
Colloidal Silica—5% by weight
Other formulation embodiments are disclosed below:
Formulation 5

| Component | Concentration Ranges |
|---|---|
| Phenolsulfonic Acid | 25-80% by weight |
| Guaiacolsulfonic Acid | 25-80% by weight |
| Ammonium Phenolsulfonate | 0-32% by weight |
| Water | 13-30% by weight |

Formulation 6

| Component | Concentration Ranges |
|---|---|
| Phenolsulfonic Acid | 25-80% by weight |
| Guaiacolsulfonic Acid | 25-80% by weight |
| Ammonium Phenolsulfonate | 0-5% by weight |
| Water | 13-30% by weight |

The formulation is applicable to the wound as a liquid or as a gel.

While specific formulations have been disclosed, it has been found that formulations having the following ranges are also suitable for use:
Formulation 7:
Formulation Containing Free Acid (Percent by Weight)
    Phenolsufonic acid (10-75% by weight)
    Guaiacolsulfonic acid (10-75% by weight)
    Free Sulfuric Acid (0-30% by weight)
    Water (0-30% by weight)
    Colloidal Silica (0-10% by weight)
Formulation 8:
Formulation with No Free Acid (Percent by Weight)
    Benzenesulfonic acid (10-75% by weight)
    Phenolsulfonic acid (10-75% by weight)
    Water (0-30% by weight)
    Colloidal Silica (0-10% by weight)

Other embodiments include method embodiments for treating chronic wounds. Chronic wounds include, but are not limited to chronic venous leg ulcers, pressure ulcers, diabetic ulcers, decubitus ulcers, stasis ulcers, dermal ulcers, burns, and pressure ulcers. Chronic wounds are characterized by necrotic tissue that delays healing.

The method embodiments include applying a formulation embodiment disclosed herein to the wound for 5 to 60 seconds. For some embodiments, a first debriding, such as mechanical debriding, is performed before adding the formulation embodiment. The method steps are repeated as appropriate. By "mechanically debride or mechanically debriding" is meant that tissue at and around a wound that is lacerated or devitalized or contaminated is removed with a mechanical device typically used in surgery such as a scissors or a scalpel or other surgical instrument.

For some embodiments, a single application of one of the formulation embodiments disclosed herein is performed. For some embodiments, the method is performed once per day until the chronic wound is healed. The term, "chronic wound" as used herein, refers to wounds such as chronic venous leg ulcers, pressure ulcers, diabetic ulcers, decubitus ulcers, stasis ulcers, dermal ulcers, burns, and pressure ulcers. Chronic wounds are characterized by necrotic tissue that delays healing and that does not heal within three months of onset.

Figure 4:
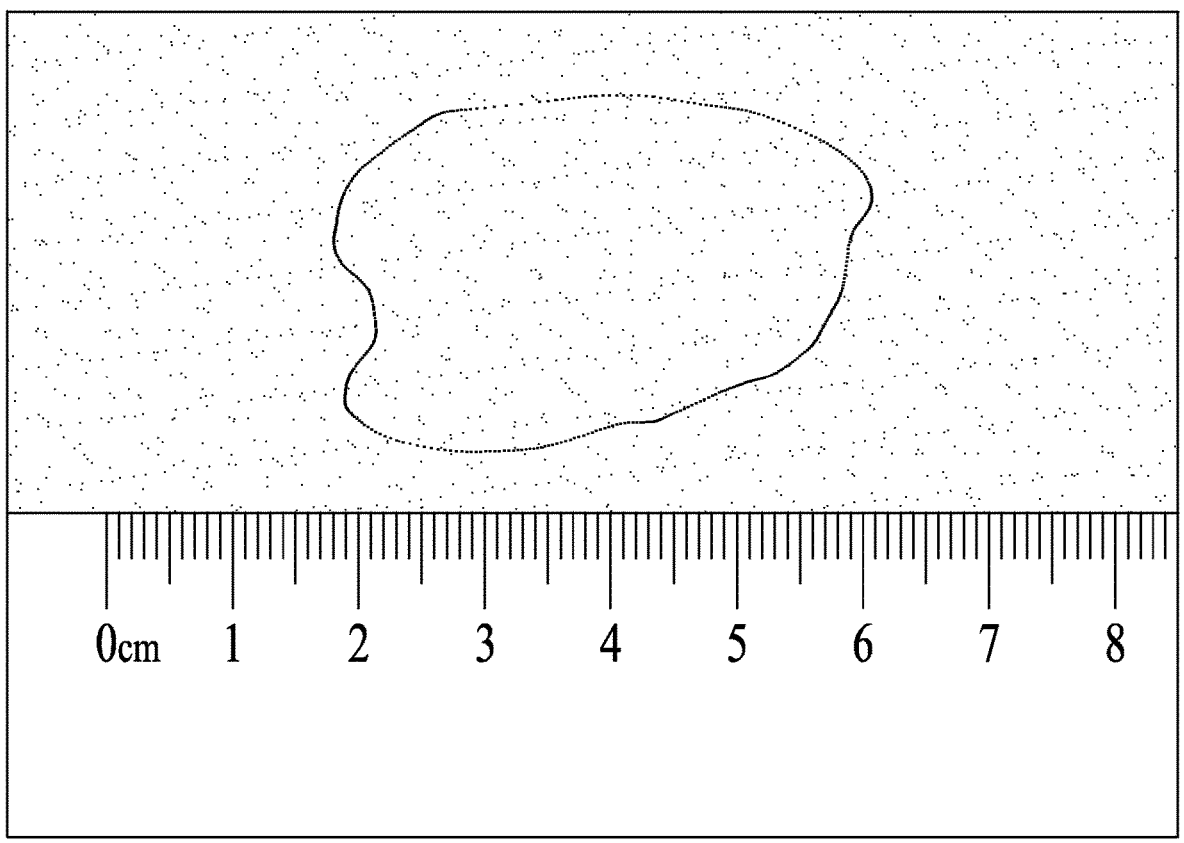
FIG. 4 is a top plan view the chronic wound of FIG. 1 three weeks after a treatment, using the formulation embodiment of the present invention used in FIG. 2. The chronic wound is healed.

In one exemplary embodiment, the formulation 6 disclosed herein was applied once to a chronic wound on the buttocks of a patient in a period of three weeks. In this treatment example, shown in FIGS. 1-4, the single exposure of the chronic wound to the formulation embodiment resulted in the wound being healed three weeks after treatment, as shown in FIG. 4. In this example, the formulation 6 was not a gel and was applied using a conventional tool. The formulation 6 was applied after a daily mechanical debridement.

The mechanical debridement includes scraping and excising tissue from a wound in order to reach healthy, viable tissue. In some instances, debridement includes cutting through edges and base of a wound in order to reach healthy tissue. The debridement is used with a scalpel, ring curette, scissors and forceps.

Since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes, which come within the meaning and range of equivalency of the claims, are intended to be embraced therein.

What is claimed is:

1. A method of treating a chronic wound, comprising:
applying a formulation to the wound for 5 to 60 seconds, the formulation comprising:
a formulation for treating chronic wounds, comprising:
benzenesulfonic acid in a concentration of 10-75% wt. percent;
phenolsulfonic acid in a concentration of 10-75% wt. percent];
water in a concentration of up to 30% wt. percent; and
colloidal silica in a concentration up to 10% wt. percent.

2. A method of treating a chronic wound, comprising:
applying a formulation to the wound for 5 to 60 seconds, wherein the wound comprises broken skin, the formulation comprising:
phenolsulfonic acid 10-75% by weight; and
guaiacolsulfonic acid 10-30% by weight;
ammonium phenolsulfonate 0-5% by weight; and
water 13-30% by weight, wherein treating the chronic wound comprises reducing the size of the chronic wound.

3. The method for treating the chronic wound of claim 2, wherein the chronic wound includes an infection by MRSA bacteria.

4. The method for treating the chronic wound of claim 2, wherein the wound comprising broken skin is one or more of a chronic venous leg ulcer, diabetic ulcer, decubitus ulcer, stasis ulcer, dermal ulcer, burn or pressure ulcer.

5. The method for treating the chronic wound of claim 2, further comprising debriding the chronic wound before applying the formulation to the wound.

6. The method for treating a chronic wound of claim 2, wherein the formulation is applied to the wound as a single application.

7. The method for treating a chronic wound of claim 2, wherein the formulation is applied once per day.

8. A method for treating a chronic wound, comprising:
Mechanically debriding the chronic wound;
Applying a formulation to the wound for 5 to 60 seconds, the formulation consisting of:
37% by weight phenolsulfonic acid;

24% by weight guaiacolsulfonic acid;
29% by weight sulfuric acid; and
10% by weight water.

\* \* \* \* \*